US009155857B2

(12) United States Patent
Lalonde

(10) Patent No.: US 9,155,857 B2
(45) Date of Patent: Oct. 13, 2015

(54) CPAP SYSTEM WITH HEAT MOISTURE EXCHANGE (HME) AND MULTIPLE CHANNEL HOSE

(75) Inventor: Michael G. Lalonde, Alpharetta, GA (US)

(73) Assignee: Human Design Medical, Inc., Allston, MA (US)

( * ) Notice: Subject to any disclaimer, the term of this patent is extended or adjusted under 35 U.S.C. 154(b) by 627 days.

(21) Appl. No.: 13/460,755

(22) Filed: Apr. 30, 2012

(65) Prior Publication Data
US 2012/0304985 A1    Dec. 6, 2012

Related U.S. Application Data

(63) Continuation-in-part of application No. 13/452,823, filed on Apr. 20, 2012, which is a continuation-in-part of application No. PCT/US2010/053370, filed on Oct. 20, 2010, application No. 13/460,755, which is a continuation-in-part of application No. 13/450,614, filed on Apr. 19, 2012, which is a continuation-in-part of application No. PCT/US2010/053370.

(60) Provisional application No. 61/253,500, filed on Oct. 20, 2009, provisional application No. 61/288,290, filed on Dec. 19, 2009, provisional application No. 61/560,271, filed on Nov. 15, 2011, provisional application No. 61/301,151, filed on Feb. 3, 2010.

(51) Int. Cl.
| A61M 16/06 | (2006.01) |
|---|---|
| A61M 16/08 | (2006.01) |
| A61M 16/10 | (2006.01) |
| A61M 16/20 | (2006.01) |
| A61M 16/00 | (2006.01) |

(52) U.S. Cl.
CPC ............ *A61M 16/06* (2013.01); *A61M 16/0069* (2014.02); *A61M 16/0875* (2013.01); *A61M 16/1095* (2014.02); *A61M 16/204* (2014.02); *A61M 16/0816* (2013.01); *A61M 16/1045* (2013.01); *A61M 16/208* (2013.01); *A61M 2016/0027* (2013.01); *A61M 2016/0033* (2013.01); *A61M 2016/1025* (2013.01); *A61M 2205/18* (2013.01); *A61M 2205/332* (2013.01); *A61M 2230/432* (2013.01)

(58) Field of Classification Search
CPC ........ A62B 18/006; A62B 7/12; A62B 18/08; A62B 9/02; A62B 9/006; A61M 16/06; A61M 16/0063; A61M 15/0086; A61M 15/0088; A61M 15/0018; A61M 15/0016; A61M 16/00; A61M 16/208; A61M 16/0069; A61F 5/56; F16K 37/0041; F16K 15/06
USPC ............ 128/204.23, 201.25, 205.12, 202.13, 128/205.17, 205.25, 207.12, 207.13, 128/200.21, 203.12, 203.29, 201.17, 848, 128/206.17, 207.11, 205.24, 204.25, 203.11
See application file for complete search history.

(56) References Cited

U.S. PATENT DOCUMENTS

| 5,301,689 A | * | 4/1994 | Wennerholm | 128/848 |
|---|---|---|---|---|
| 5,372,130 A | * | 12/1994 | Stern et al. | 128/205.25 |
| 5,438,981 A | * | 8/1995 | Starr et al. | 128/205.24 |

(Continued)

*Primary Examiner* — Annette Dixon
(74) *Attorney, Agent, or Firm* — Ascentage Law, PLLC

(57) ABSTRACT

A continuous positive airway pressure (CPAP) system provides positive airway pressure therapy. It has been recognized that users generally prefer to breathe freely rather than to fight the pressurized air when possible. A continuous positive airway pressure (CPAP) system provides positive airway pressure therapy when required, but allows the user to breathe freely with the mask on when positive airway pressure is not required. The system has a valve that moves between two positions to open and close the unassisted breathing vent and the outlet from the flow generator.

16 Claims, 20 Drawing Sheets

(56) References Cited

U.S. PATENT DOCUMENTS

| | | | |
|---|---|---|---|
| 5,542,416 A * | 8/1996 | Chalvignac | 128/204.23 |
| 5,896,857 A * | 4/1999 | Hely et al. | 128/205.24 |
| 8,439,035 B2 * | 5/2013 | Dantanarayana et al. | 128/205.24 |
| 2006/0157056 A1 * | 7/2006 | Burk | 128/201.13 |
| 2012/0266873 A1 * | 10/2012 | Lalonde | 128/201.13 |

* cited by examiner

CPAP SYSTEM WITH HEAT MOISTURE EXCHANGE (HME) AND MULTIPLE CHANNEL HOSE

CROSS-REFERENCE TO RELATED APPLICATIONS

This application is a continuation-in-part of U.S. patent application Ser. No. 13/452,823 filed on Apr. 20, 2012 which is a continuation-in-part of PCT Application PCT/US2010/053370 filed on Oct. 20, 2010 which claims the benefit of U.S. Patent Application 61/253,500 filed on Oct. 20, 2009, U.S. Patent Application 61/288,290 filed on Dec. 19, 2009, and U.S. Patent Application 61/301,151 filed on Feb. 3, 2010 and claims the benefit of U.S. Patent Application 61/560,271 filed on Nov. 15, 2011, which are incorporated herein by reference. In addition this application is a continuation-in-part of U.S. patent application Ser. No. 13/450,614 filed on Apr. 19, 2012 which is a continuation-in-part of PCT Application PCT/US2010/053370 filed on Oct. 20, 2010 which claims the benefit of U.S. Patent Application 61/253,500 filed on Oct. 20, 2009, U.S. Patent Application 61/288,290 filed on Dec. 19, 2009, and U.S. Patent Application 61/301,151 filed on Feb. 3, 2010 and claims the benefit of U.S. Patent Application 61/560,271 filed on Nov. 15, 2011, which are incorporated herein by reference.

TECHNICAL FIELD

The present invention relates to a gas delivery system, and more particularly to a positive pressure gas delivery system with a mask with a heat moisture exchange (HME) and that allows a user to breathe when the pressurized gas is not being provided to the mask. The system in certain embodiment has a hose with multiple channels.

BACKGROUND INFORMATION

Certain individuals have difficulty breathing during sleep due to a collapse or obstruction of airways. For example, obstructive sleep apnea (OSA) may occur when the body relaxes during sleep, and the upper airway of the sleeping individual collapses, either partially or completely, to obstruct breathing during sleep. This condition is particularly common in overweight individuals, individuals with large necks, or individuals who abuse alcohol.

One treatment for the above-noted condition is the application of a continuous positive airway pressure apparatus (CPAP). It is recognized that a blower can be mounted as part of a unit carried on the head such as shown in International Application PCT/US2010/053370, which is incorporated herein by reference.

BRIEF SUMMARY OF THE INVENTION

It has been recognized that users generally prefer to breathe freely rather than fighting the pressurized air when possible. However, the user needs to have the mask on at certain times such as sleeping so that the system can provide pressurized air when required. The mask as described allows the user to both breathe freely when possible and switch modes when pressurized air is required.

A continuous positive airway pressure (CPAP) system provides positive airway pressure therapy when required, but allows the user to breathe freely with the mask on when positive airway pressure is not required. The system has a valve that moves between two positions to open and close the unassisted breathing vent and the outlet from the flow generator.

In an embodiment of a gas delivery system that provides positive airway pressure therapy during a user's sleep period, the system has a mask that couples to a user's face to deliver pressurized gas to an airway of the user. In an embodiment, the mask includes a flow generator system that pressurizes gas from ambient air. The flow generator system includes at least one motor. The mask has a washout vent that allows fluid communication, separately from the flow generator system, between the exterior of the mask and the interior of the mask. The mask has an unassisted breathing vent that allows fluid communication, separately from the flow generator system and the washout vent, between the exterior of the mask and the interior of the mask. A check-valve in the mask obstructs the unassisted breathing vent during operation of the flow generator.

In an embodiment, the system has a heat moisture exchange through which the air from the flow generator system passes to condition the air for the user.

In an embodiment, the check-valve moves to a position therein redirecting the path of the air from the flow generator system through the HME and a second position wherein the air from the at least one unassisted breathing vent bypasses the HME.

In an embodiment, the check-valve moves between a compressor mode position blocking the at least one unassisted breathing vent and a free breathing position blocking the outlet from the flow generator.

In an embodiment, the check-valve is biased to the free breathing position blocking the outlet from the flow generator and is forced to the compressor mode position by the pressure from the flow generator.

In an embodiment, the flow generator is spaced from the mask. A hose is interposed between the flow generator and the mask for conveying pressurized gas to the mask. The check-valve is located on the mask.

In an embodiment, the washout vent area is less than 20 percent of the area of the at least one unassisted breathing vent.

A method of treating sleep apnea of a user utilizes a mask having a seal to engage a face of the user defining a cavity adapted to overlie at least one of the user's mouth and user's nose. The mask has a port for receiving pressured gas created from the ambient air. The mask has a wash out vent for expelling of gases, including carbon dioxide, to the exterior of the mask. Gas is capable of communicating from the cavity of the mask to the exterior of the mask through at least one unassisted breathing vent. A flow generator, also referred to as a compressor, pressurizes the gas for delivery to the cavity for positive airway pressure (PAP) therapy to the user.

The unassisted breathing vent is closed by moving a check-valve to obstruct the unassisted breathing vent during operation of the flow generator. The check-valve is moved to a second position allowing communication of gas from the cavity to the exterior of the mask through at least one unassisted breathing vent when the flow generator is turned off.

The check-valve is biased to the free breathing position blocking the outlet from the flow generator and is forced to the compressor mode position by the pressure from the flow generator.

These aspects of the invention are not meant to be exclusive and other features, aspects, and advantages of the present invention will be readily apparent to those of ordinary skill in the art when read in conjunction with the following description, appended claims, and accompanying drawings.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

A continuous positive airway pressure (CPAP) system provides positive airway pressure therapy. The system described has a mask that is coupled to a user's face to deliver pressurized gas to an airway of the user. The system has a flow generator system that pressurizes gas. The flow generator system includes at least one motor. The system has a washout vent that allows fluid communication, separately from the flow generator system, between an interior of the mask and an exterior of the mask. The system has an unassisted breathing vent that allows fluid communication, separately from the flow generator system and the at least one washout vent, between an exterior of the mask and an interior of the mask. A check-valve carried by the mask obstructs the at least one unassisted breathing orifice during operation of the flow generator.

The abbreviation CPAP stands for continuous positive air pressure which in generic terms is a method of noninvasive or invasive ventilation assisted by a flow of air delivered at a positive pressure throughout the respiratory cycle. It is performed for patients who can initiate their own respirations but who are not able to maintain adequate arterial oxygen levels without assistance. Sometimes the word "continuous" is replaced with the "constant." For the purpose of this patent, constant positive airway pressure is referred to as mono-level CPAP. CPAP can be in various modes including mono-level CPAP, Bi-level CPAP, Auto-PAP, Servo-ventilation, and ramping. The pressure can also be varied in each pressure mode mentioned to range from 0 pressures to 50 cm $H_2O$ pressure.

Figure 1:
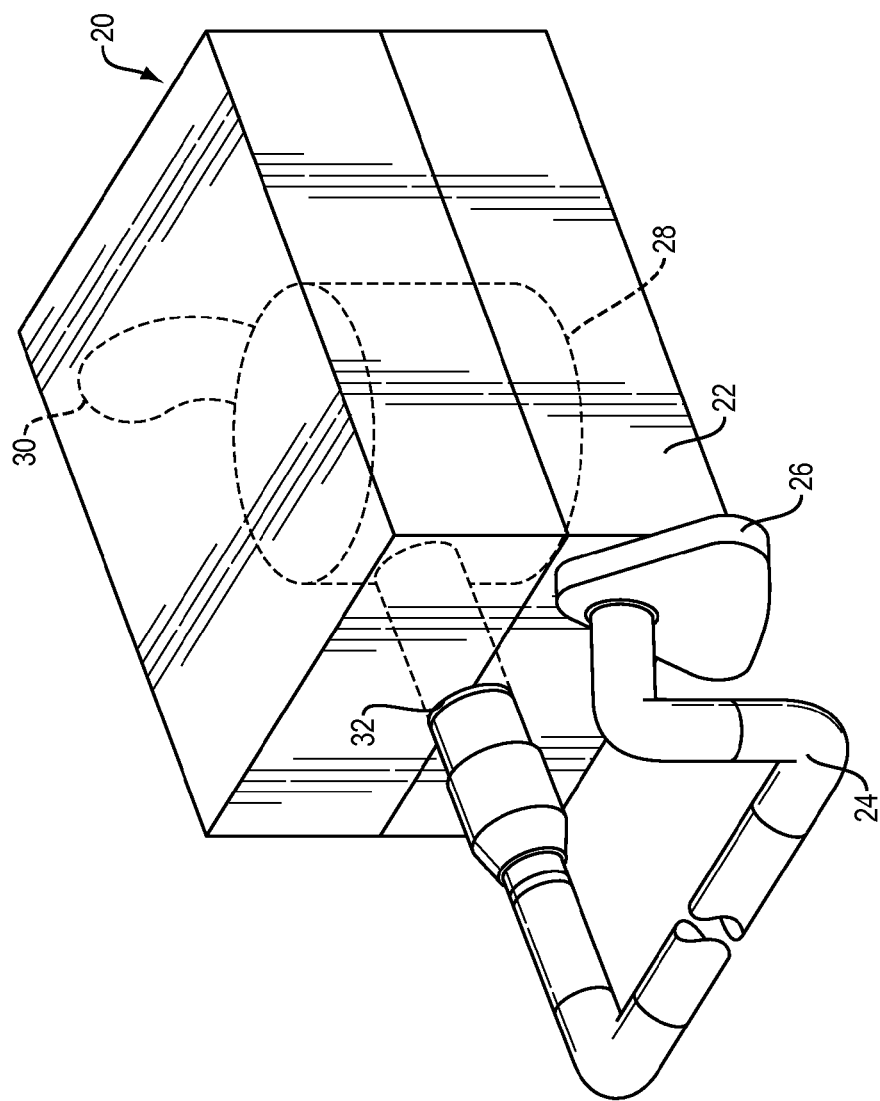
FIG. 1 a perspective view of a continuous positive air pressure (CPAP) system.

Referring to FIG. 1, a perspective view of a continuous positive air pressure (CPAP) system 20 is shown. The system 20 has a flow generator 22 that is connected by a connector 24 to a mask 26 to provide pressurized air. In the embodiment shown, the connector 24 is a hose. CPAP systems 20 are used to treat apnea. In OSA (Obstructive Sleep Apnea), the upper airway collapses and blocks airflow during sleep. The collapse can occur at several points, for example the soft palate in the upper oropharyngeal or pharynx level is drawn downward into the throat during sleep and blocks the airway; the orientation of the user and gravity effects can influence the percentage of blockage.

The flow generator 22 has a compressor 28, shown in hidden line, which gathers air from an inlet 30 and compresses the air to increase the pressure. The air, also referred to as compressed gas, exits the compressor 28 and flows through a connector interface 32.

The abbreviation CPAP stands for continuous positive air pressure which in generic terms is a method of noninvasive or invasive ventilation assisted by a flow of air delivered at a positive pressure throughout the respiratory cycle. It is performed for patients who can initiate their own respirations but who are not able to maintain adequate arterial oxygen levels without assistance. Sometimes the word "continuous" is replaced with the "constant." For the purpose of this patent, constant positive airway pressure is referred to as mono-level CPAP. CPAP can be in various modes including mono-level CPAP, Bi-level CPAP, Auto-PAP, Servo-ventilation, and ramping. The pressure can also be varied in each pressure mode mentioned to range from 0 pressures to 50 cm $H_2O$ pressure.

Figure 2:
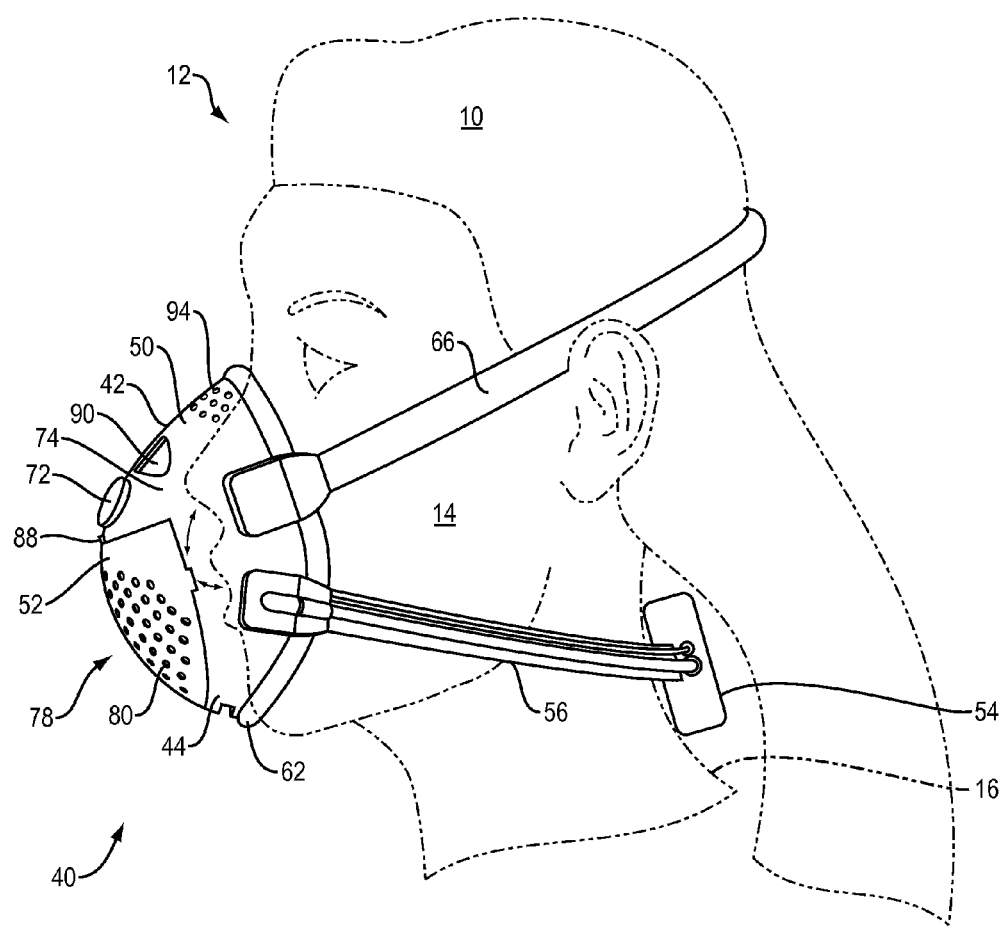
FIG. 2 is a perspective view of an integrated CPAP system.
Figure 3:
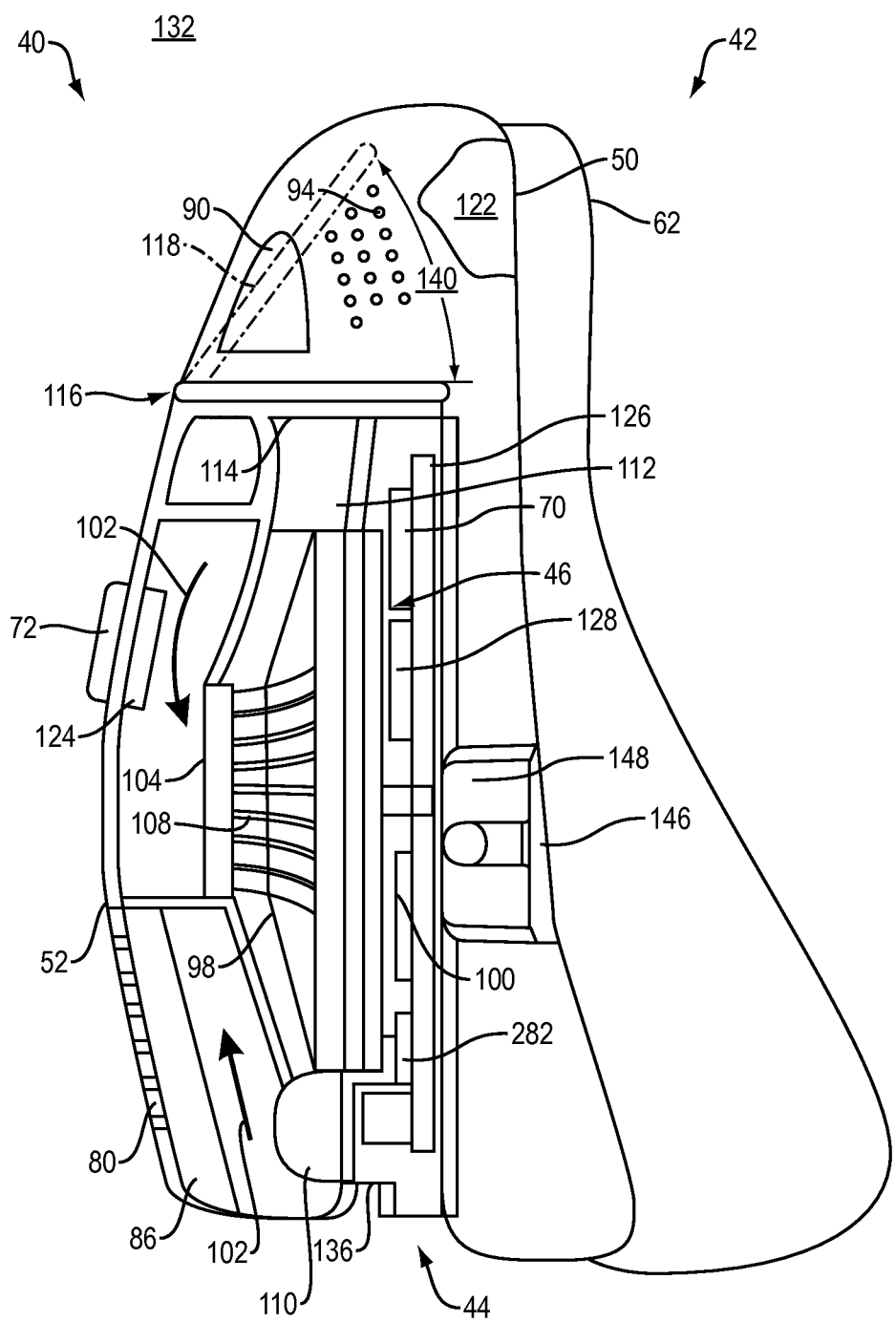
FIG. 3 is a section view of the CPAP unit having an integrated compressor and free breathing apparatus.

Referring to FIG. 2, a section view of an integrated CPAP system 40 with an integrated CPAP unit 42 including a mask 44 on a face 14 is shown. The CPAP system 40 includes a flow generator 46, as seen in FIG. 3, which is connected to a rigid mask shell 50. The flow generator 46 is covered with a flow generator cap 52.

In the embodiment shown, a power supply enclosure 54, which may include batteries, is connected via a strap 56 to the integrated CPAP unit 42. The strap 56 may be adjustable such that the power supply enclosure 54 may be supported at the back of a user's neck 16. While shown on the back of the neck 16, it is recognized that the power supply 54 can be located at other locations such as the arm, shoulder, hip, chest, or integrated with the CPAP unit 42.

The integrated CPAP unit 42 is configured to couple to the user's face 14. In this regard, the mask 44 has a user interface cushion 62 typically comprised of a pliant material. In one example, the compliant material includes silicone, gel, foam, or another such compliant material and is configured to form a relatively gas-tight interface between the remainder of the integrated PAP unit 42 and the user's face 14.

In addition to the strap 56 which has the power supply 54, the system 40 has an upper strap 66 to assist in securing the mask 44 to the user's face 14. Typically, the upper strap 66 is adjustable and/or elastic to adjust to the circumference of the user's head 12.

The integrated CPAP unit 42 depicted in FIG. 2 may include a controller 70 as seen in FIG. 3. The unit 42 has a control button 72 for easy access by the user wearing the integrated CPAP unit 42 to allow the user at a minimum to power on and off the unit 42. In one embodiment, the control button 72 is disposed on the upper area 74, typically aligned with the nasal area of the patient. However, other areas may be convenient, depending on the user's preferences, and the location of the control button 72 is not limited to the upper part of the integrated CPAP unit 42.

Still referring to FIG. 2, ambient air will travel through a flow generator intake flow path 78 past a plurality of orifices 80 such as flow generator intake holes 80. The flow generator intake holes 80 may be, in turn, disposed on the flow generator cap or flow generator intake door 52. One benefit of this arrangement is that the flow generator intake holes 80 may be changed in size by replacement of the flow generator intake door 52. Another benefit of this arrangement is that the flow generator intake door 52 can be opened occasionally to replace an intake filter 86, as seen in FIG. 3. In one example, the flow generator intake door 52 is connected to the remainder of the integrated CPAP unit 42 via a flow generator intake door latch 88.

Figure 5:
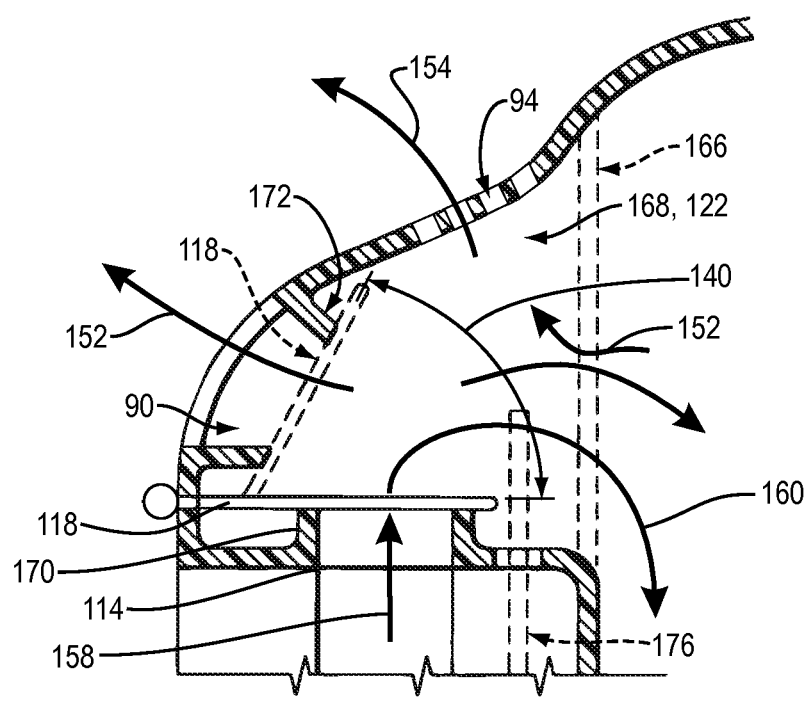
FIG. 5 is a section view taken along lines 5-5 in FIG. 4.

The integrated CPAP unit 42 has an unassisted breathing vent 90 which allows the user to breathe freely. The unassisted breathing vent 90 is opened and closed by a gas flow diverter 116 as explained in detail with respect to FIGS. 3 and 5. Additionally, the integrated CPAP unit 42 typically includes a plurality of washout vents 94 which are continually operable. In other words, the $CO_2$ washout vents 94 remain open during normal operation of the integrated CPAP unit 42 and even when not in operation. The washout vents 94 are sized so that the pressurized gas created by the flow generator 46 is maintained at a sufficient level in the interior of the mask as the washout vents 94 allow gas to exit an interior or mask chamber 122/168 as seen in FIG. 5 of the mask 44 as represented by arrow 154.

It is recognized that the unit 42 can provide a variety of CPAP treatment modes which provide variability of pressurized gas delivery which are widely known to those skilled in the art, that of, continuous single pressure (continuous), two pressure levels responding alternately to certain respiratory inputs of the patient (Bi-level), auto-adjusting pressure also based on certain respiratory inputs of the patient (Auto-set), and servo-ventilation mode which varies pressure to match certain characteristics of the breathing rhythm (Auto-servo).

Referring to FIG. 3, a sectional side view of the integrated CPAP unit 42 of the integrated CPAP system 40 is shown. The flow generator 46 of the integrated CPAP unit 42 has a compressor 48 which includes a motor 98 and an impeller 100 to generate the increase in pressure between the ambient air and the gas supplied to the user 10 shown in FIG. 2.

The flow generator 46 draws ambient air through the intake filter 86 disposed inside the flow generator intake door or cap 52. The air then typically travels through a tortuous path 102 that may include some form of sound-abatement device such as an acoustic damper to an opening 104 overlying the impeller 100. The flow generator 46 increases the pressure of the air. As the air spins off the impeller 100 by the blades 108 of the impeller 100 it is collected in a collection chamber 110 which encircles the blades 108 of the impeller 100. The collection chamber 110 opens into an expansion chamber 112. The expansion chamber 112 ends at the outlet 114 of the flow generator 46. The outlet 114 is capable of being covered by a diverter flap 118 of a check valve 116.

Figure 4:
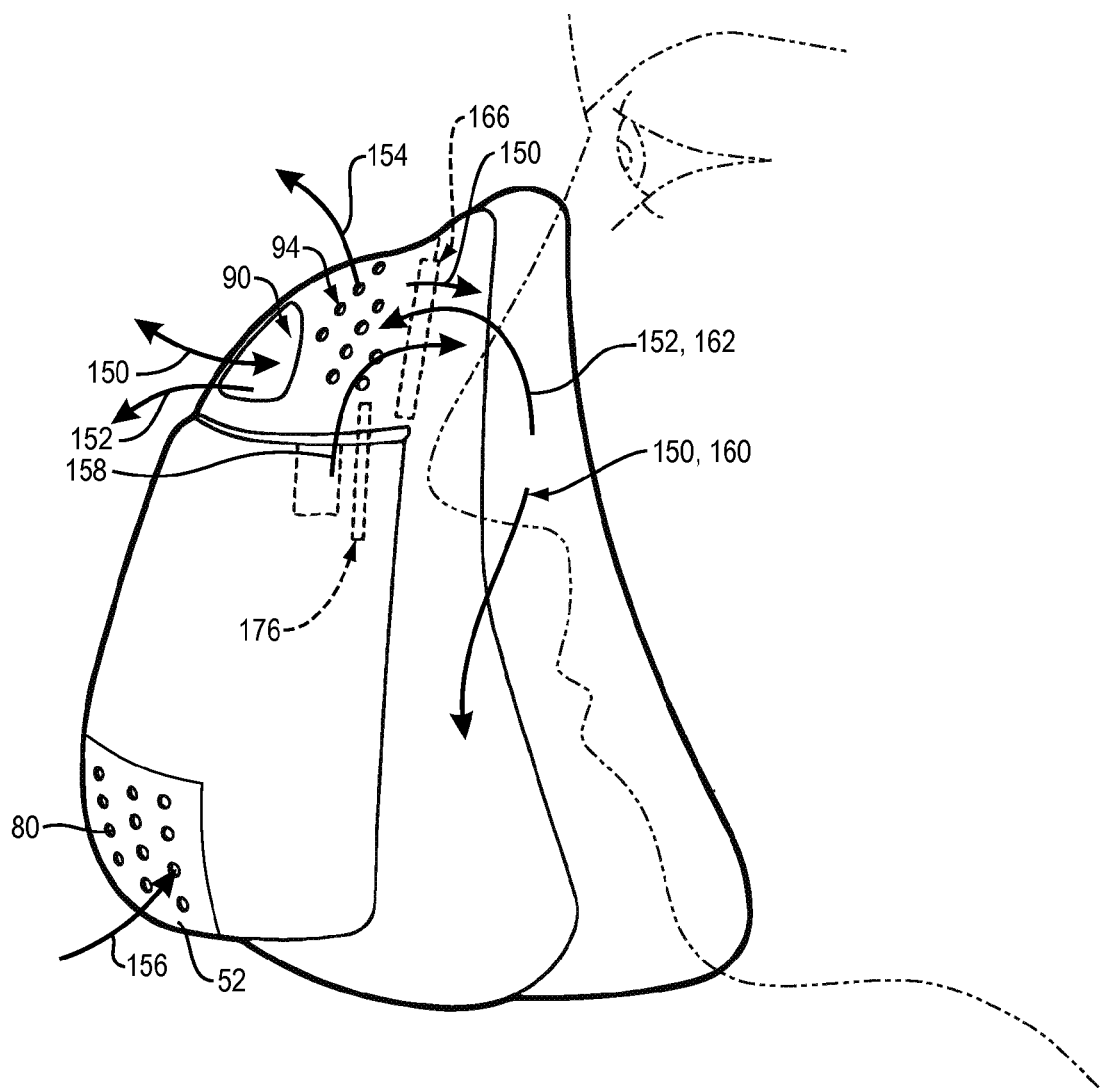
FIG. 4 is a schematic representation of a gas flow path of the CPAP unit depicted in FIG. 3.

The controller 70 of the integrated CPAP unit 42 is interposed between the impeller and the interior/dead air space 122 as seen in FIG. 4. The control button 72 of the unit 42 that allows for easy access by the user wearing the integrated CPAP unit 42 to allow the user at a minimum to power on and off the unit 42 has a small printed circuit board (PCB) 124. The small PCB 124 is connected to a larger PCB 126 that contains the controller 70 via a connector, which is not shown in the FIG.

In one embodiment shown, the motor 98 has a plurality of stators 128 that are mounted on the PCB 126. The motor 98 has a magnet 130 which underlies the impeller 100 and rotates with the impeller 100. The stators 128 are parallel with the PCB 126.

The integrated CPAP 42 can be powered by various methods including a battery in the power supply enclosure 54 shown in FIG. 1 or connected to a power source. The integrated CPAP unit 42 has a power and data connector receptacle 136. The power and data connector receptacle 136 may be connected to an AC adaptor or automobile circuit adaptor to provide power in place of the power supply, such as a battery, within the power supply enclosure 54. One benefit of this arrangement is that a practically unlimited supply of power may be available by replacing the power supply 54, and even though the user 10 is somewhat tethered to the AC adaptor or automobile circuit adaptor, the connection between these components and the power and data connector receptacle 136 is relatively thin in comparison to the hose used in typical CPAP apparatuses. Therefore, the user 10 typically has a greater sense of freedom when using the integrated CPAP unit 42 in comparison to conventional CPAP units.

In the embodiment shown, the integrated CPAP unit 42 has the check valve 116 controlling flow between an interior and exterior of the unit 42 via the unassisted breathing vents 90. In one embodiment, the check valve 116 includes a diverter flap 118 that travels along a path 140 to open and close the outlet of the flow generator 46. In the upper position along the path 140, the diverter flap 118 closes the unassisted breathing vents 90 which is also referred to as a compressor mode position.

In addition to the compressor mode position, the diverter flap 118 has a second position, a free breathing position when the diverter flap 118 is in a relaxed position covering the outlet 114 from the compressor 48; this position occurs when the compressor 48 is off.

When the compressor 48 which is part of the flow generator 46, is in operation, the pressure generated by the flow generator 46 pushes the diverter flap 118 against the unassisted breathing vents 90, the compressor mode position, thus closing the vents 90; the user 10 receives the air that has been pressurized by the flow generator 46. When the user 10 exhales, the pressure in the interior 122 of the mask 44 increases from the combination of the air from the flow generator 46 and the user exhaling breath therein creating an increased pressure differential between the interior 122 of the mask 44 and the exterior 132 of the mask 44; this increase in the pressure differential results in a greater flow rate of expired gases to escape through the washout vents 90 to the outside 132 of the integrated CPAP unit 42. At all times while pressure is created by the flow generator 46, the diverter flap 118 of the check valve 116 is forced open. When the flow generator 46 does not provide sufficient pressure to force the diverter flap 118 open, unassisted breathing vents 90 are uncovered and the user 10 can freely breathe through these vents or ports 90. The unassisted breathing vent 90 allows direct communication between the interior 122 of the integrated CPAP unit 42 and the exterior 132 of the integrated CPAP unit 42 when the diverter flap 118 of the check valve 116 is in the free breathing position, closing the outlet 114 to the flow generator 46.

Still referring to FIG. 3, a portion of the rigid mask shell 30 of the mask 24 and a portion of the user interface cushion 42 are shown. The straps 36 and 46 shown in FIG. 1 have a plurality of tabs that are received by a slot 146 in a pivotable housing 148.

Referring to FIG. 4, a schematic representation of the mask 44 is shown. The arrows 150 show the air flow as the user inhales, also referred to as inspiration, during "unassisted" or "free" breathing. The air is drawn through the unassisted breathing vent 90. As the user exhales, also referred to as expiration, the air flows out of the unassisted breathing vent 90 as represented by the arrow 152 and also out of the washout vents 94 as represented by the arrow 154.

Still referring to FIG. 4, when the flow generator 46 is running, the air, as represented by arrows 156, is pulled through the orifices 60 on the flow generator cap 52 into the tortuous path 102 to the flow generator 46, as seen in FIG. 3, to the interior 122 of the mask 44 via the outlet 114 of the compressor 48 as represented by the arrow 158. As the user inhales, the pressurized air in the interior 122 of the mask 44 is drawn into the mouth and/or nose of the user as represented by arrow 160. As the user exhales, the air flows out of the washout vents 94 as represented by the arrows 162 and 154.

The integrated CPAP unit 42 has a membrane/heat exchanger 166 through which the air/gas passes as the gas flows from either the unassisted breathing vent 90 or the outlet 114 of the flow generator 46 toward the patient's face, i.e., the nasal area or mouth. The gas picks up moisture that has been retained on the membrane 166 from the user 10 exhaling through the membrane 166.

Referring to FIG. 5, a section view of the mask showing a chamber 168 of the interior 122 with the washout vents 94 and the unassisted breathing vent 90 is shown. The chamber 168 of the integrated CPAP unit 42 has a compressor exhaust flap seat 170 that abuts the diverter valve flap 118 in order to close the outlet 114 of the flow generator 46. This state of the diverter valve flap 118 is typical when the pressure generated by the compressor cannot overcome the elastic resistance of diverter valve flap 118, for example, when the compressor 48 of the flow generator 46 is turned off. This diverter valve may also be deployed with a spring, spring tension clip, a diaphragm, or other such method known to those skilled in the art.

Still referring to FIG. 5, the diverter valve flap 118 is shown in phantom in an "up" position when the pressure is supplied by the flow generator 46, which provides an abutment contact between an unassisted breathing vent valve seat 172 and the diverter valve flap 118. In this state of the diverter valve flap 118, the patient exhales through the $CO_2$ wash-out vents 94. Arrow 140 shows the movement of the diverter flap 118.

Figure 6:
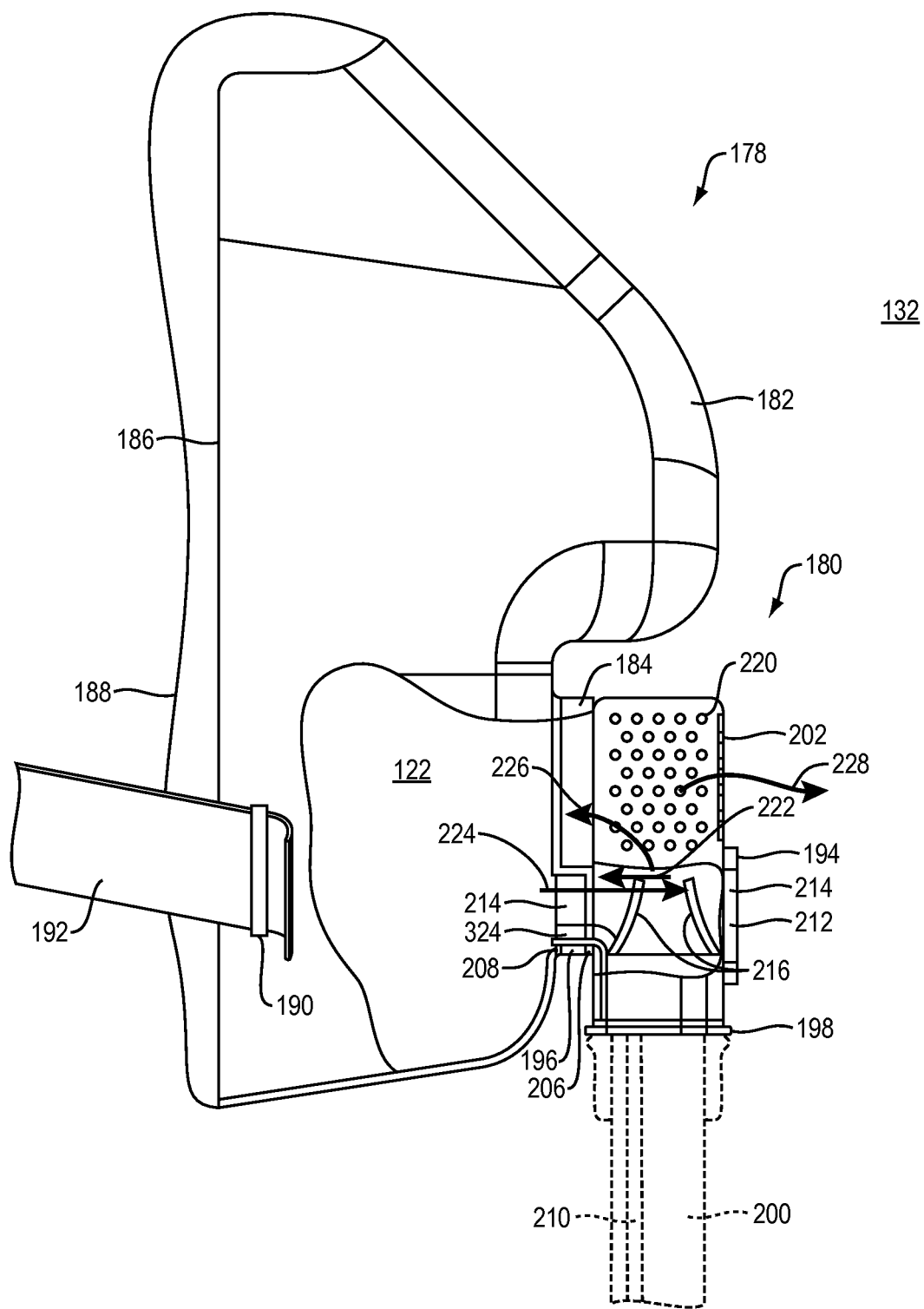
FIG. 6 is a side view of an alternative mask with a portion broken away.
Figure 7:
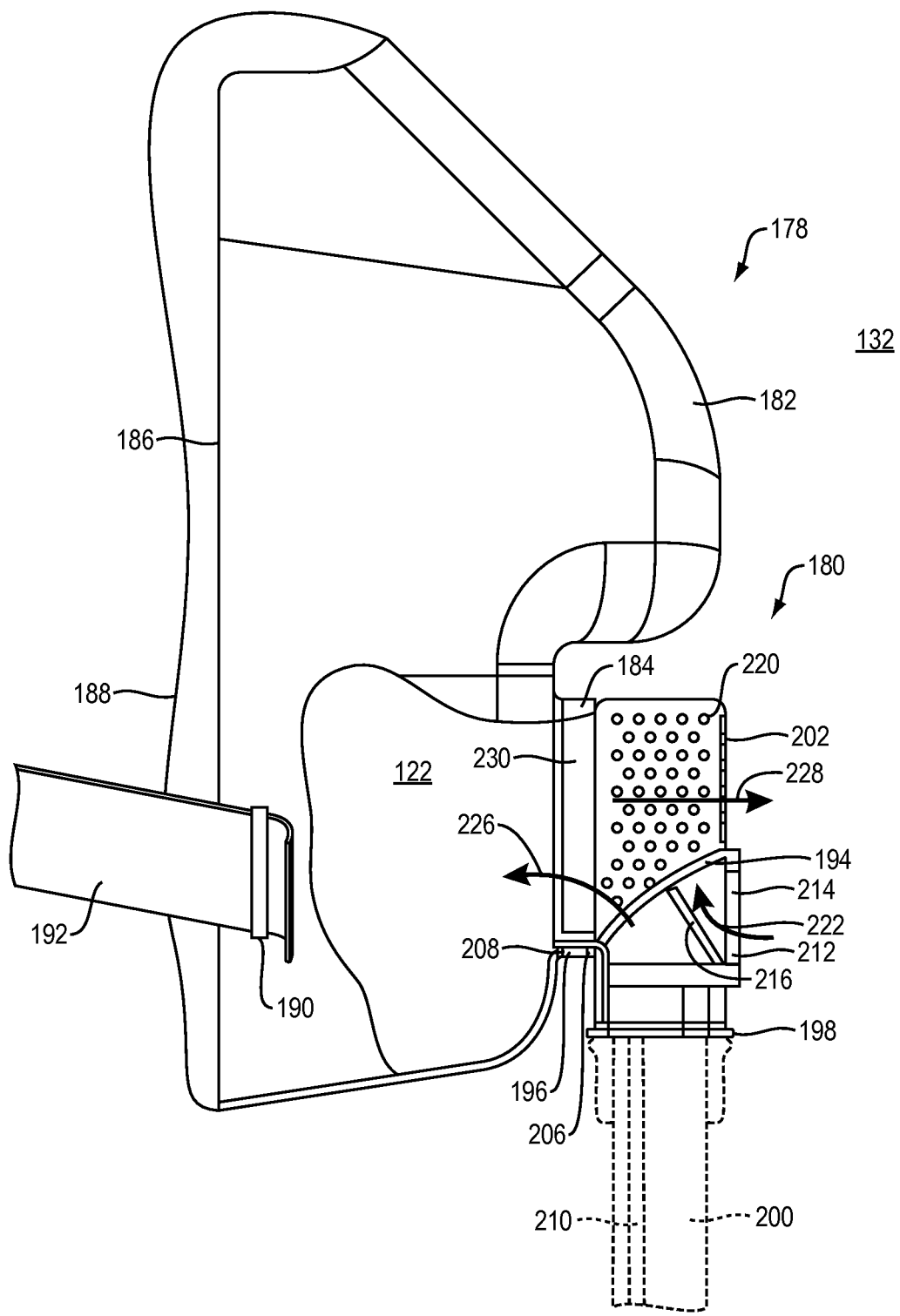
FIG. 7 is a side view of an alternative mask with a different arrangement of the HME.

Referring to FIG. 6, a sectional view of a portion of the mask 180 of an alternative system 178 is shown. In this embodiment, the flow generator 22 is separated from the mask 180 by a connector, a hose 200 which is described in further detail with respect to FIGS. 15-19. The mask 180 has a shell or frame 182 with a gas inlet aperture 184. The shell 182 has a rim portion 186. The mask 180 has a pliable portion 188 such as a cushion or gel portion that is received on the rim portion 186 of the shell 182. The frame 182 has a plurality of connection points 190 for connecting a plurality of straps 192 to retain the mask 180 to the user's face.

The mask 180 has a mask connector 194 with a connector 196 that interfaces with the gas inlet aperture 184. The mask connector 194 has an interface 198 for receiving a hose 200 for receiving pressurized gas from a separate blower unit that has the compressor that creates the compressed air.

In addition, the mask 180 has a suitable exhaust port or washout vents 202 for exhausting breathing gases during expiration/exhalation.

The washout vents 202 are continuously-open ports which impose a suitable flow resistance upon the exhaust gas flow. In an embodiment, this allows the system to permit a pressure controller system 206 including a port 208 in the mask, a conduit 210, shown in hidden line, through the hose 200 to a pressure sensor which through a controller located in the separate blower unit controls the pressure of the air flow from the compressor to the mask 180.

In one embodiment, the washout vents 202 may be of sufficient cross-sectional flow area to sustain a continuous exhaust flow of approximately 15 liters per minute. The flow via the washout vents 202 is one component, and typically the major component of the overall system leakage, which is an important parameter of system operation.

Still referring to FIG. 5, the mask 180 has a free breathing system 212 that is open when the compressor is not providing pressurized air at a specific rate. The free breathing system 212 includes a plurality of the unassisted breathing vents 214 and a pair of diverter flaps 216 that cover the unassisted breathing vent 214 when pressurized air is flowing from the hose 200 to the mask connector 194.

Still referring to FIG. 5, the system 162 has a heat moisture exchange (HME) component 220. The HME component 220 carried by the mask connector 194 collects moisture as the user's exhalation that passes through the washout vent 202, also referred to as the exhaust port. As the user receives pressurized air from the blower unit through the mask connector 194, the pressurized air flows through the HME 220 to an interior or cavity 122 with the shell 182 of the mask 180 therein providing moisture to the air.

In contrast to the embodiment shown in FIGS. 3-5, the user is not required to breathe through the HME 220 when in the free breathe mode. The path of the air during inhale free breathing is shown by arrow 222. The path of the air during exhaling during free breathing is shown by arrow 224. A portion of the air flow passes through the HME 220; however the flow path through the HME 220 has a higher resistance.

When the system 162 is in the compressor mode position, the diverter flap 206 blocks the unassisted breathing vents 204. The path of the air during inhalation is shown by arrow 226. The path of the air during exhalation when the compressor is on is shown by arrows 228.

Still referring to FIG. 5, a sensor board 176 is disposed downstream of the compressor 48 and may be used to monitor a parameter such as pressure, flow, temperature, $O_2$ level, $CO_2$ level, etc. While the sensor board 176 is shown partially above the diverter flap 118 and in the inhale and exhale breathing pathway, it is recognized that the same or additional sensors can be located in the compressor 48 expansion chamber, prior to the outlet 114 and the diverter flap 118.

Referring to FIG. 6, a sectional view of a portion of the mask 180 of an alternative embodiment is shown. In contrast to the embodiment shown in FIG. 5 where a portion of the air flow from the compressor 28 does not flow through the HME 220, the entire air flows through the HME 220. The opening 220 into the interior 80 of the mask 180 can be shaped and sized to tailor the air flow both when using the flow generator 22 and the unassisted breathing vent 214.

Figure 8:
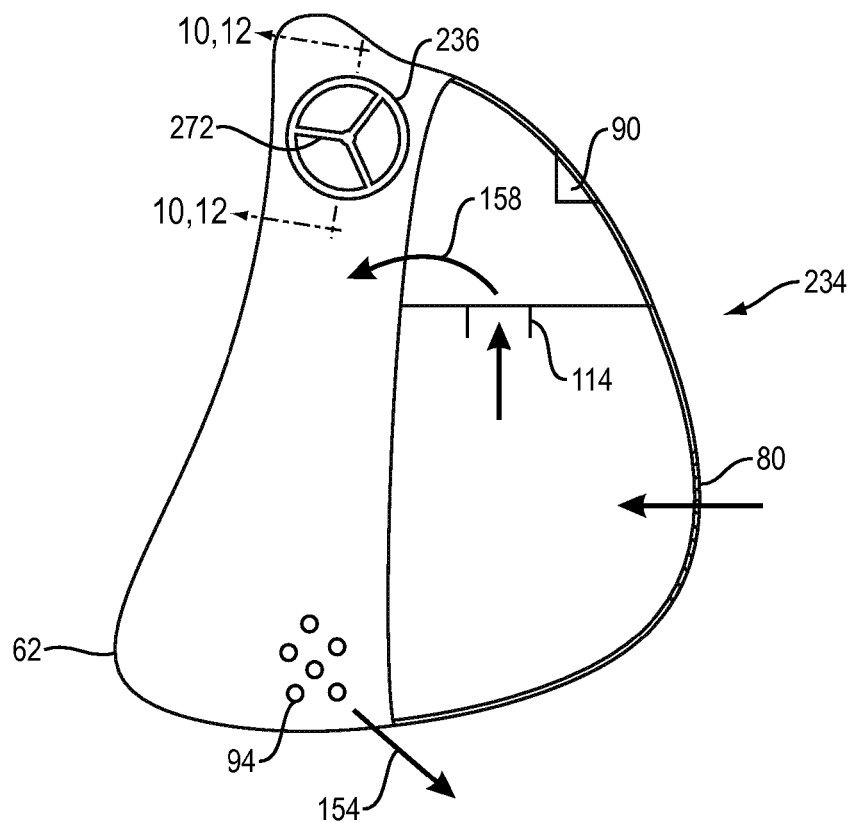
FIG. 8 is a side view of an alternative mask with an anti-asphyxiation valve.

Referring to FIG. 8, a side view of an alternative mask 234 with an anti-asphyxiation valve 236 is shown. When the integrated CPAP system 40 uses the integrated CPAP unit 42, the air for the flow generator 46 is drawn in the orifices 80 located on the front of the mask 44 as shown on FIGS. 2, 3, & 4. The anti-asphyxiation valve 236 is located at a different location on the mask 234 than the orifices 80 and the free breathing opening 90.

The mask 234 of the integrated CPAP system 40 affixes to a user's face with a mask interface 62. The ambient air is drawn into the flow generator 46 through the orifices 80. The flow from the flow generator 46 exits the outlet 114 as best seen in FIG. 5, in the direction of arrow 158. As indicated above, the exhaust gases, including $CO_2$, exit the washout vents 94. The anti-asphyxiation valve 236 in this embodiment is designed to open when the mask 234 is oriented in a specific orientation.

Figure 9:
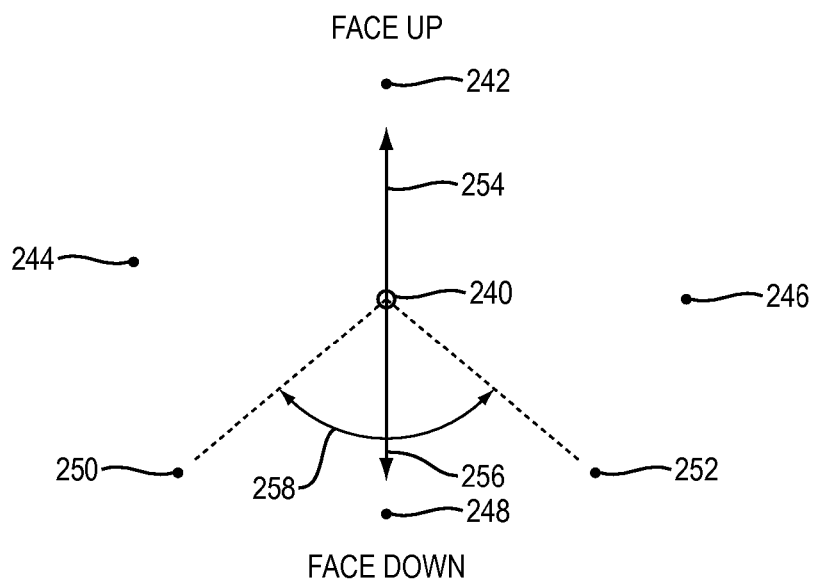
FIG. 9 is a graphical representation of the orientation of the mask of FIG. 8.

Referring to FIG. 9, a graphical representation of the orientation of the mask 234 is shown. The mask 234 is represented by a point 240 at the origin of the plot. When the mask 234 is orientated upward, such as on a face 14 of a user 10 lying on their back, it is represented by a point 242 and arrow 254. When a user 10 is lying on their side, the orientation is represented by points 244 and 246. When a user 10 is lying on their chest such that her/his face is facing downward is represented by a point 248 and arrow 256. In addition, FIG. 9 shows a range represented by arrow 258 from a point 250 to a point 252 which are a certain angle of a user 10 having their face 14 facing downward.

Figure 10:
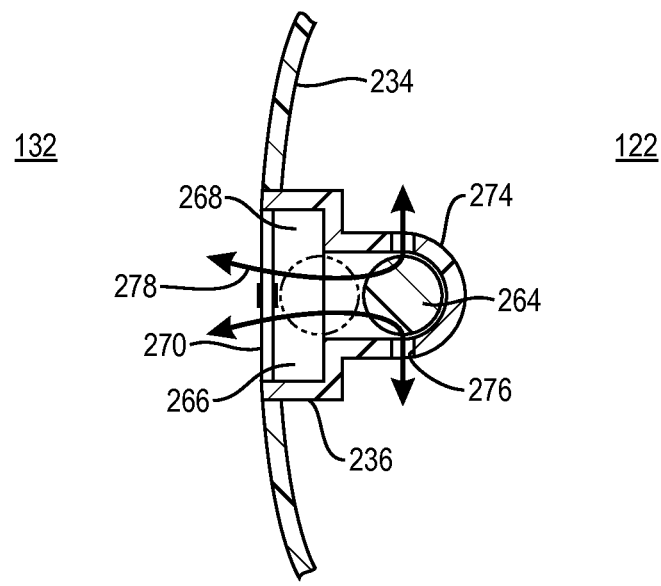
FIG. 10 is a sectional view taken along the line 10-10 in FIG. 8.

Referring to FIG. 10, a sectional view 10-10 of the anti-asphyxiation valve 236 is shown. The valve 236, a ball valve, has a ball 264 that is captured in a chamber 266 having an enlarged square-shaped containment area 268 at one end that is open to the exterior 132 (environment). The valve 236 has a retainer 270 which consists of three arms 272, as best seen in FIG. 8, to prevent the ball 264 from falling out of the chamber 266. The other end of the chamber 266 is defined by a round-shaped containment 274 with a plurality of holes 276 that open onto the interior 122. When the ball 264 is blocking the holes 276, no air can escape from the interior 122 of the mask 234 to the exterior 132. When the ball 264 is in the open position, as seen in phantom, the gases from the interior 122 of the mask 234 can flow freely by way of air flow path 278. The retainer 270 obstructs the ball 264 from escaping but also permits air to pass.

When the mask 234 is orientated between points 250 and 252 of FIG. 9, that is with the mask 234 facing downward, the ball 264 rolls to the position shown in phantom in FIG. 10 and air can flow between the exterior 132 and the interior 122 of the mask 234 along flow path 278. When the user 10 is in the position between 250 and 252 including position 242, the ball 264 is in the closed position shown in FIG. 10.

Figure 11:
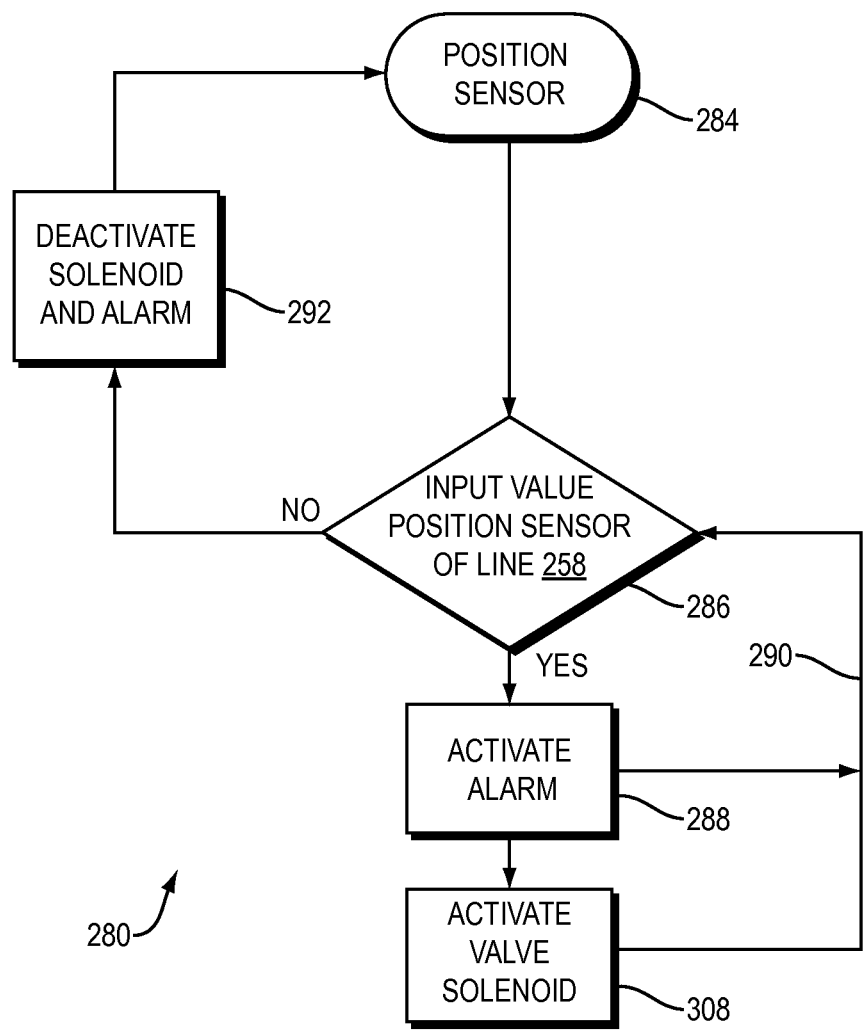
FIG. 11 is a schematic of a method of setting of the alarm.

Referring to FIG. 11, a schematic for creating an alarm if the mask 234 is in a certain orientation is shown. The mask 234 has a position sensor, such as an accelerometer 282 shown in FIG. 3, and represented by block 284 in FIG. 11. The system 280 determines if the mask 234 is in the range as represented by line 258 by the "yes" branch of decision diamond 286. The system 280 activates the alarm as represented by block 288. The system 280 continues to monitor as represented by the arrow 290 back to the decision diamond 286. If the system 280 determines that the mask 234 is out of the range as represented by line 258 as represented by "no" branch of the decision diamond 286, then the system 280 deactivates the alarm and solenoid, if it exists, as represented by block 292.

Figure 12:
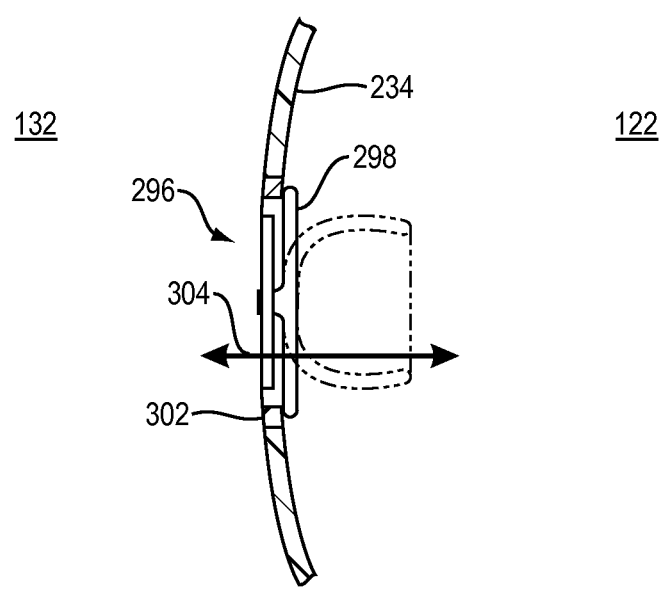
FIG. 12 is an alternative embodiment sectional view of the valve of FIG. 8.

Referring to FIG. 12, an alternative embodiment sectional view of a valve 296 of FIG. 8 is shown. The valve 296 has a diaphragm 298 that is biased to a position shown in phantom. When the diaphragm 298 is forced closed by the pressure on the interior 122 of mask 234, the diaphragm 298 engages a sealing edge 302 on the mask 234. When the pressure in the interior 122 of the mask 234 is less than the pressure of the exterior 132, the environment, the diaphragm 298 returns to the open position shown in phantom permitting air to flow as represented by an arrow 304.

It is recognized that a solenoid can be attached to the valve shown in FIG. 12 to open and close the valve. The solenoid is attached to a shaft of the valve. The valve is seated in a valve seat when in the closed position. The ambient/environment air is resisted by the closed valve. When open, the solenoid is activated and it extends the valve allowing air to flow freely through the valve. The solenoid valve is controlled by a control which outputs to the alarm as represented by block 288 and the valve solenoid as represented by block 308 in FIG. 11 with inputs from the motion sensor 282 in FIG. 3.

The opening and closing of the valve by a solenoid can be done by various methods. One method is based on the orientation of the mask 234. Referring back to FIG. 11, if the "yes" branch of decision diamond 286 is followed in addition to activating the alarm as represented by block 288, the valve solenoid is activated as represented by block 308. The system 280 continues to monitor the orientation to control the opening and closing of the valve solenoid.

Figure 13:
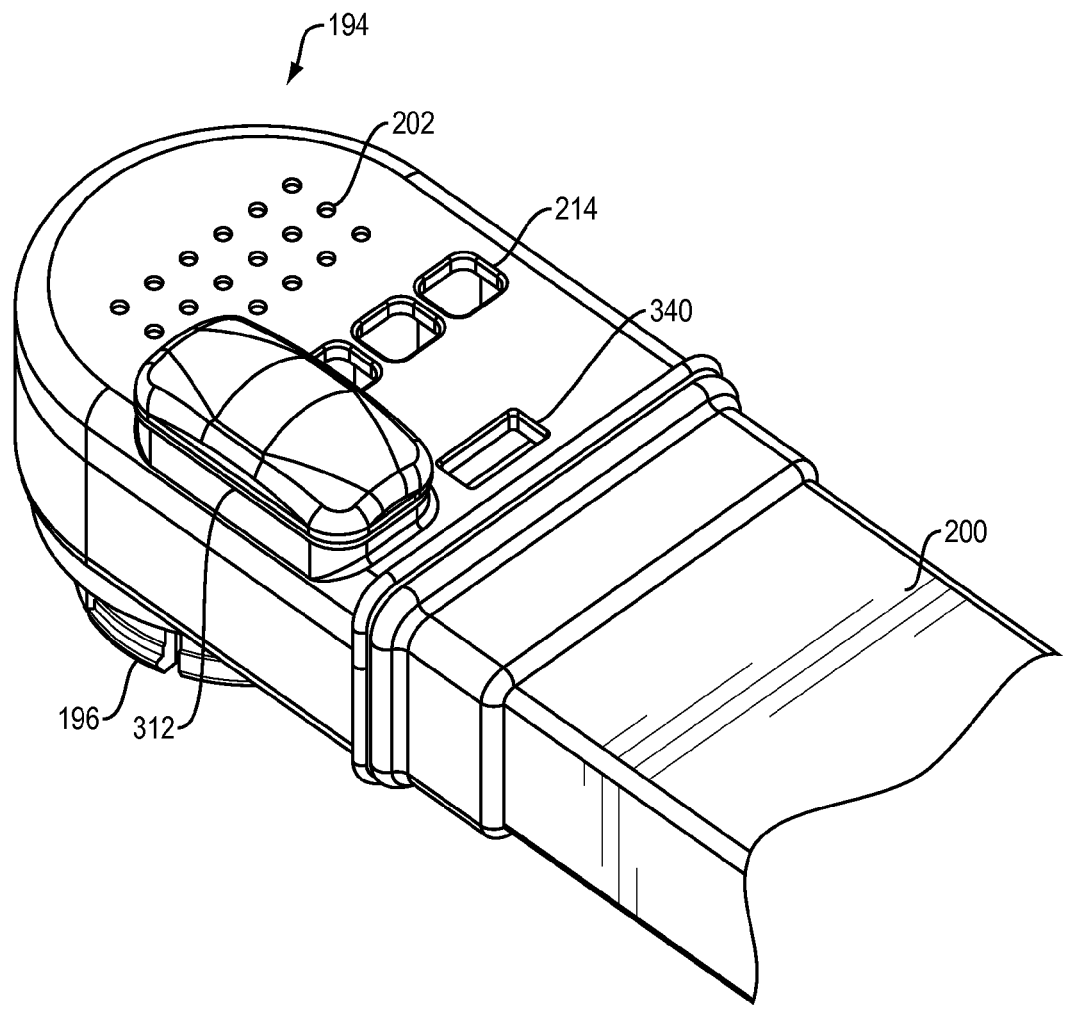
FIG. 13 [2B] is a perspective view of the hose and the mask connector.

A conventional CPAP system uses a circular hose 24 as the connector between the flow generator 22 and the mask 26. Referring to FIG. 13, a perspective view of the mask connector 194, as seen in FIG. 6, and a low profile hose 200 is shown. The mask connector 194 has the exhaust port 202 and the breathing port 214. In addition, the mask connector 194 has a button, a switch, which is connected to a pressure switch located on the flow generator 22 for turning on the compressor 28.

Figure 14A:
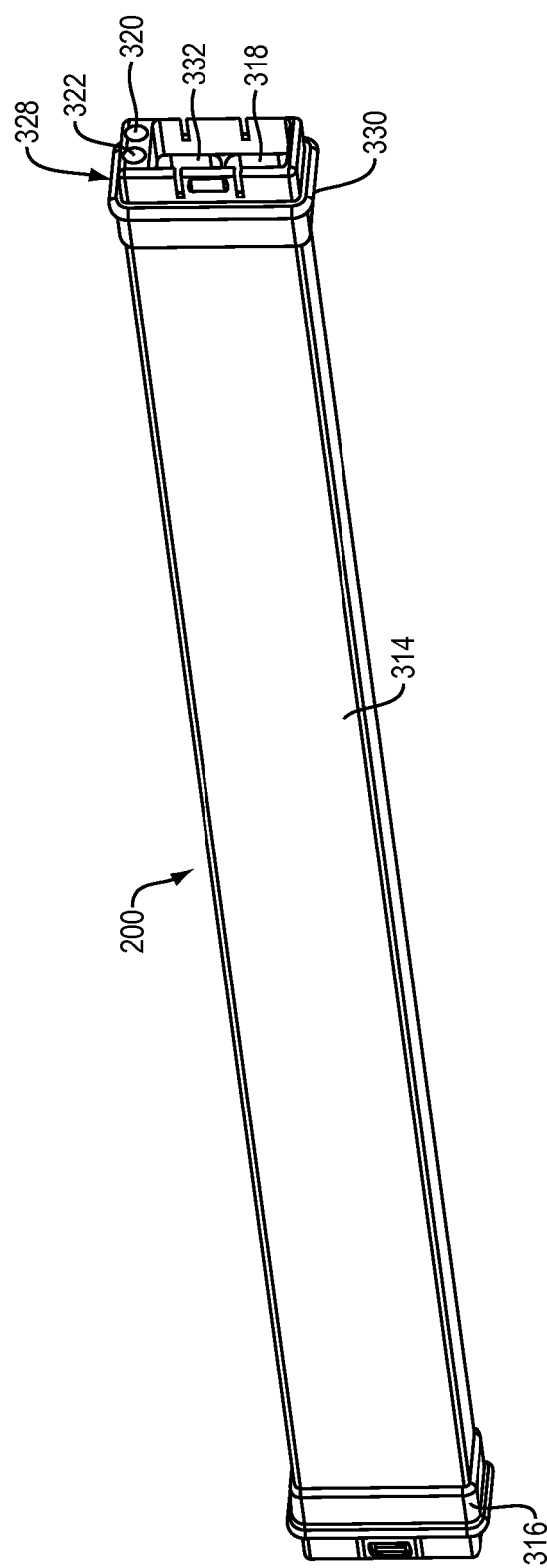
FIG. 14A [6A] is an isometric view of a hose.

Referring to FIG. 14A, an isometric view of the hose 200 is shown. The hose 200 has a tube (hosepipe) 314 and a hose connector 316 at each end. The hose 200 has a pair of air flow channels 318 for communicating the pressurized air from the flow generator 22 to the mask 26 as seen in FIG. 1. In addition, the hose 200 has a pair of communication channels 320 and 322. In the embodiment shown, one of the communication channels 320 connects the button 312, as seen in FIG. 13, on the mask 24 and the pressure switch to allow the user to turn the system 178 from a stand-by mode to operation. The other communication channel 322 connects a port 324, as seen in FIG. 13, on the mask 24 with a pressure sensor located on a printed circuit board (PCB) in the flow generator 22; the pressure sensor monitors the flow and allows a controller to adjust parameters.

Figure 14B:
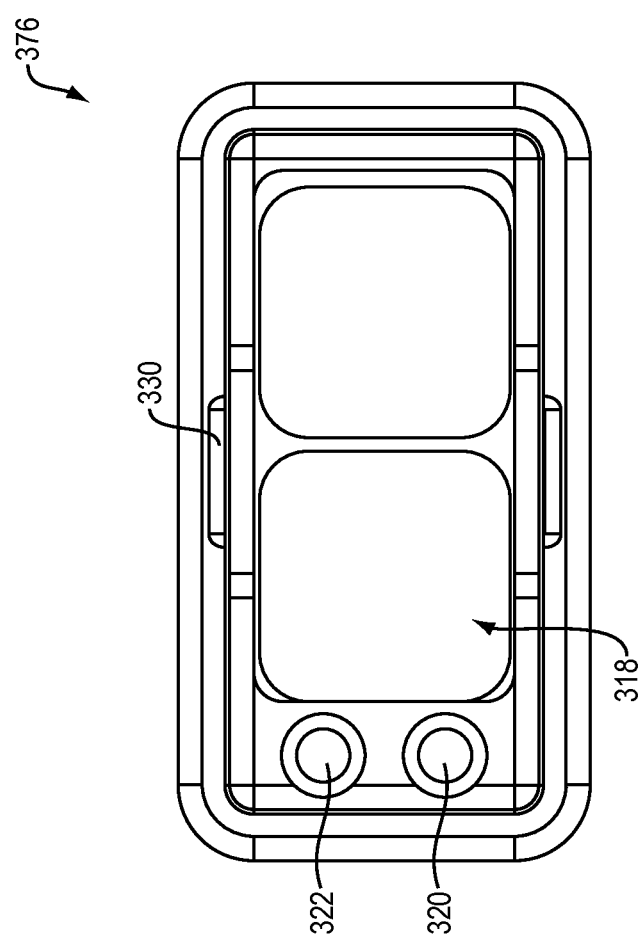
FIG. 14B is a side view of the hose.
Figure 14C:
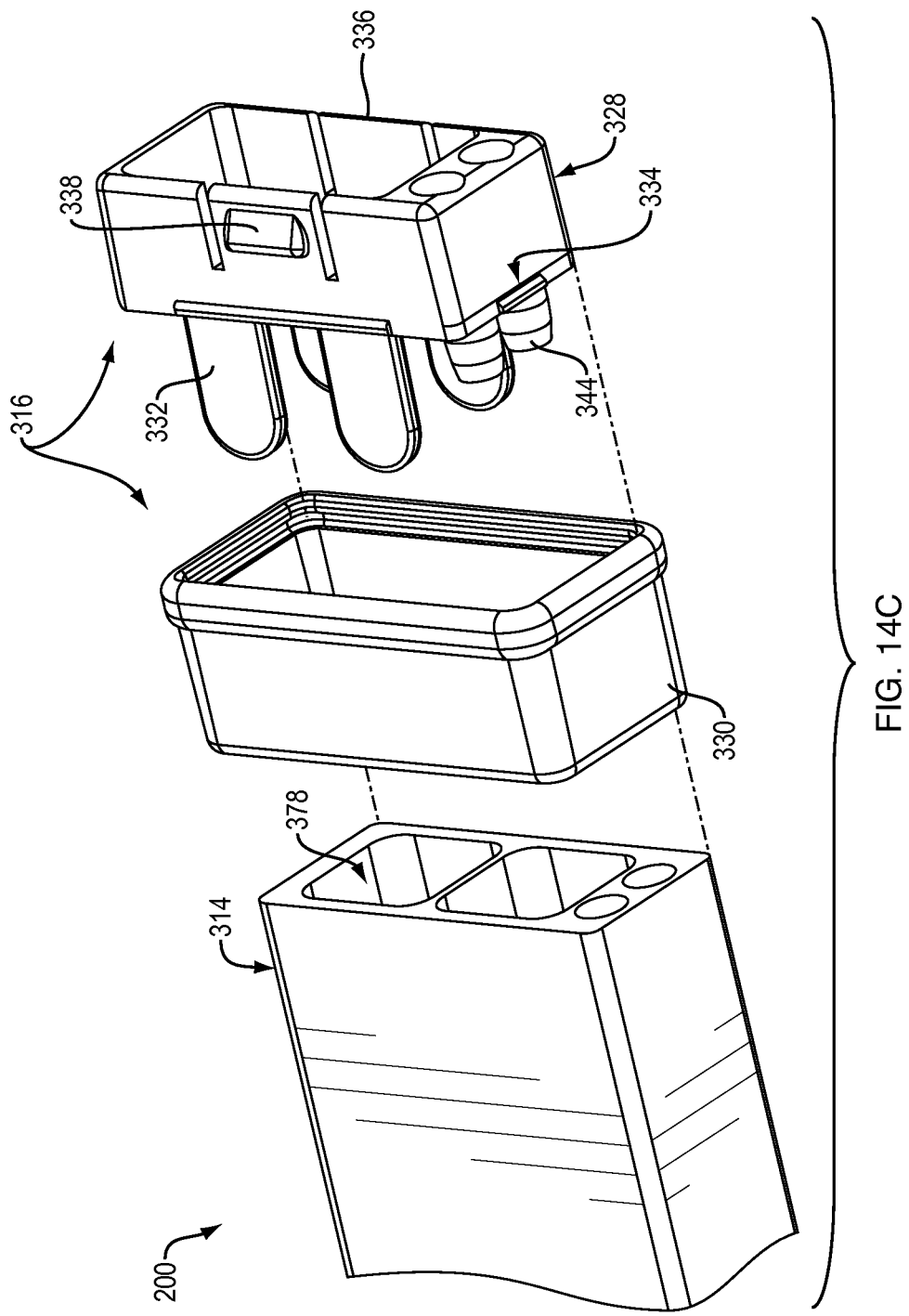
FIG. 14C is an exploded view of the hose with the two components of the hose connectors separated.

FIG. 14B is a side view of the hose 200 showing one of the hose connectors 316. FIG. 14C shows the hose 200 exploded with the two components of the hose connector 316 separated. The hose connector 316 has a mating portion 328 and an outer sleeve 330. The mating portion 328 has a plurality of tabs 332 that are received in the flow channels 318 of the hosepipe 314. The outer sleeve 330 encircles the edge of the hosepipe 314 and has a groove to receive a ridge 334 located on the mating portion 328 to assist in securing the components. The mating portion 328 has a pair of tabs 336. Each tab 336 has a detent 330 that is received in one of the detent openings 340 located on the hose interface connector of the flow generator 22 or on the mask connector 194 as seen in FIG. 13B. The projections 238 as seen in FIG. 4 are received in communication channels 278 and 280. The mating portion 282 has projections 298 which are received in the respective openings in the hosepipe 272

Figure 15:
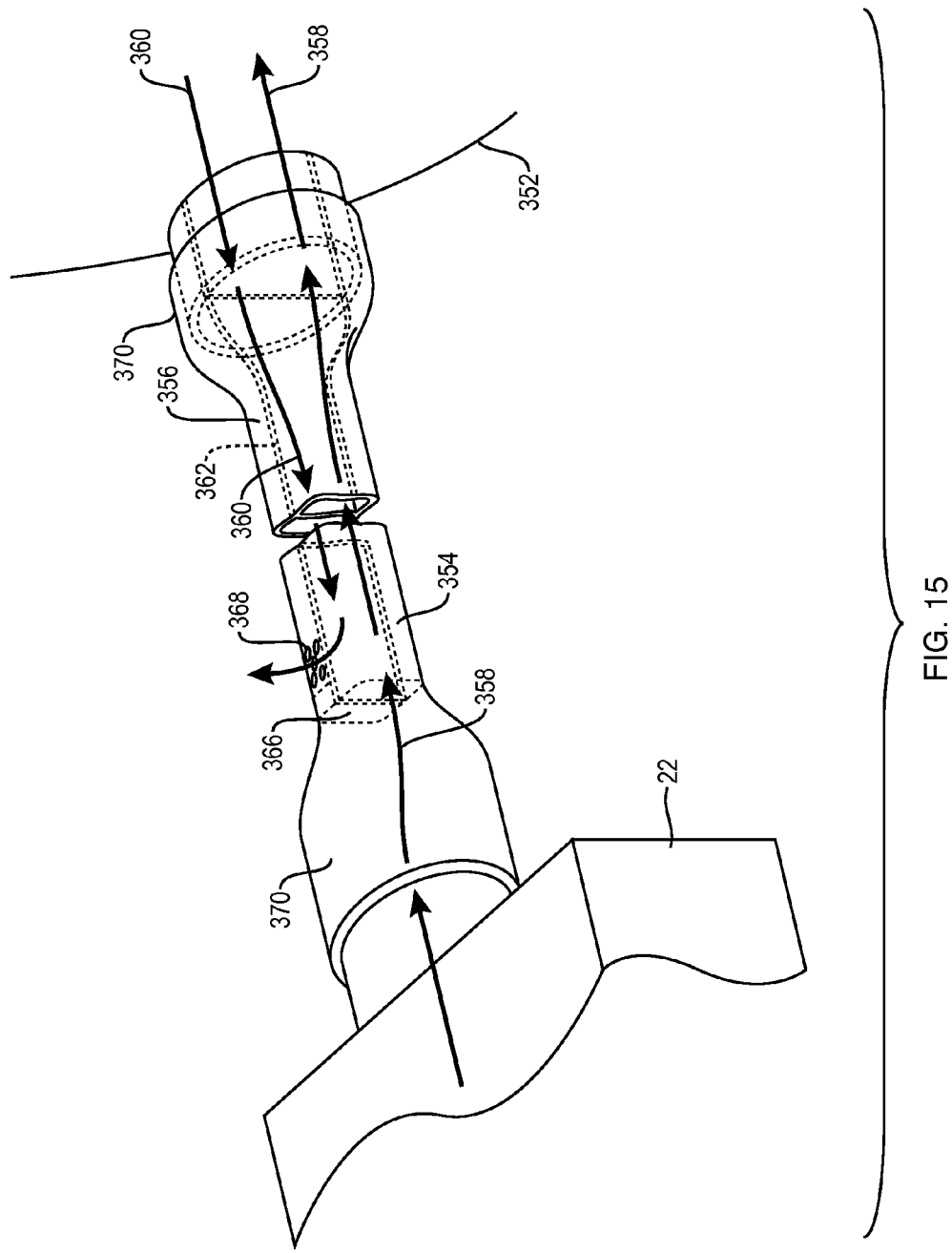
FIG. 15 is a perspective view of a hose from the flow generator to a mask having two way flow.

In the embodiment shown in FIGS. 13-14C, the hose 200 is used to send the compressed gas from the flow generator 22 to the mask 26; the gas exhaled from the user 10 is vented at the mask 26. Referring to FIG. 15 a perspective view of an alternative hose 350 from the flow generator 22 to a mask 352 having two-way flow is shown. The hose 350 has two air flow channels 354 and 356, similar to those shown in FIG. 14B and FIG. 14C; however, the air flow as represented by arrows 358 in one of the flow channels 354 is from the flow generator 22 to the mask 352 and the air flow as represented by arrows 360 in the other flow channel 356 is in the opposite direction. The hose 350 has a wall 362 between the pair of air flow channels 354 and 356 which in addition to providing support allows the flows to be in opposite directions. Rather than the mask 352 having washout vents 94 located on the mask, such as on the mask 44 in FIG. 3, the exhaled air from the user 10 flows down the second communication channel 356 in the direction of the flow arrows 360 towards the flow generator 22. The second channel 356 has a blockage 366 that prevents the exhaled air from reaching the flow generator 22. The hose 350 has a series of vent holes 368, similar to the washout vents 94 on the mask 44 in FIG. 3, to allow the $CO_2$ to vent. One of the purposes of moving the washout vents 94 off of the mask is to reduce air noises near the face 14. The size of the channels 354 and 356 are sized for the requirements and would be larger than those shown in FIG. 14C. In addition, while only two channels 354 and 356 are shown it is recognized that there can be multiple channels in both directions. In the embodiment shown, the hose 350 has a connector 370 at each end which transitions from the hosepipe rectangular shape to a circular shape of standard type connections.

Figure 16:
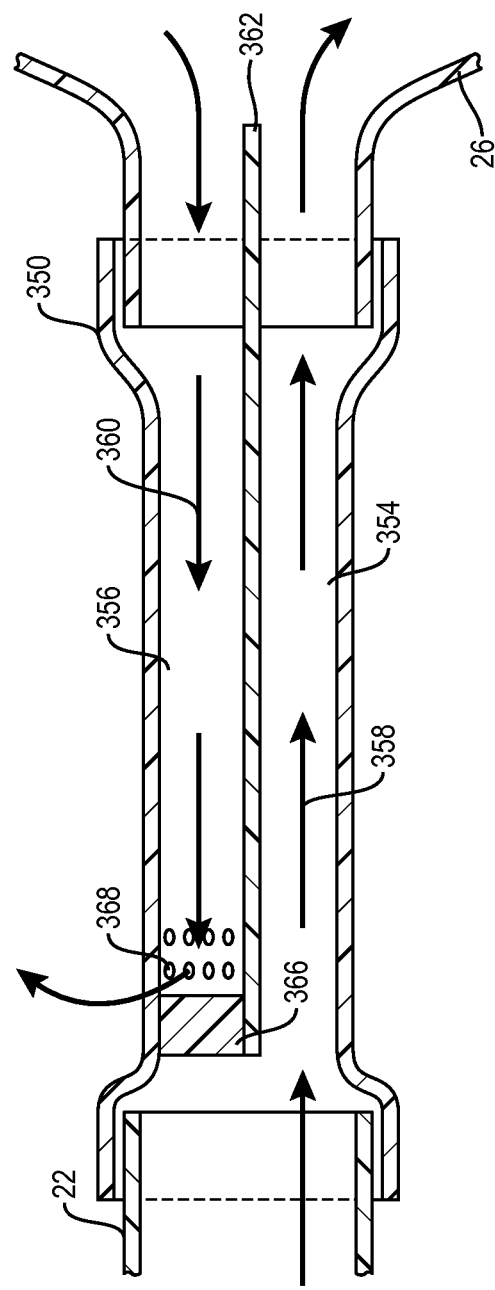
FIG. 16 is a sectional view of the hose of FIG. 15.

Referring to FIG. 16, a sectional view of the hose 350 of FIG. 15 is shown. The bottom channel, the first communication channel 354, of the hose 350 as in the FIG. has compressed air flowing from the flow generator 22 to the mask 352 as represented by the flow arrows 358. The second communication channel 356, the upper channel in the FIG., of the hose 350 has a flow of exhaust gas as represented by the arrows 360. The exhaust gas is vented out the vent holes 368 in the hose 350. The blockage 366 prevents the exhaust gas from reaching the flow generator 22. The mask 352 has a channel that connects the interior 122 of the mask 352 where exhaled gases would gather to the hose 350 connection.

Figure 17:
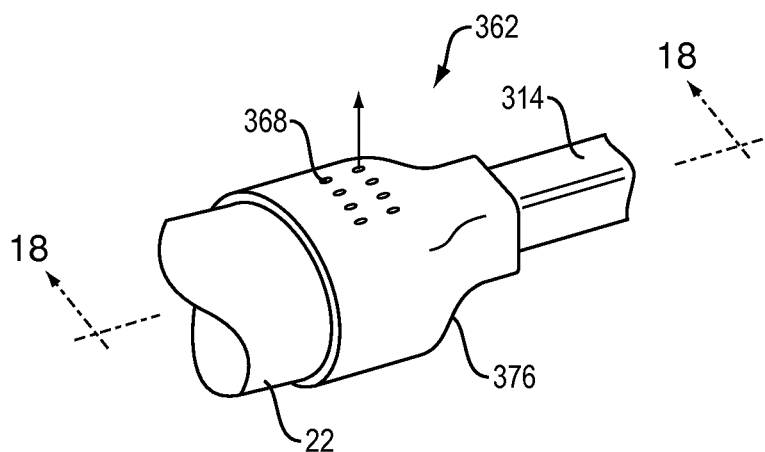
FIG. 17 is a perspective view of a connector.
Figure 18:
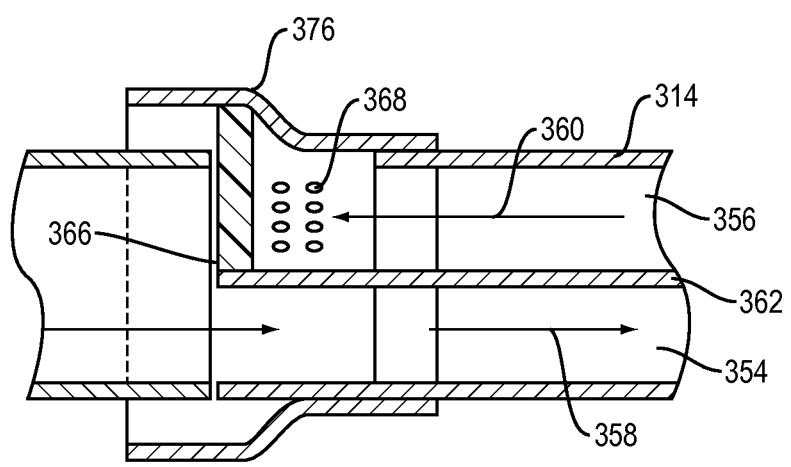
FIG. 18 is a sectional view of the connector of FIG. 17 taken along the line 18-18.

Referring to FIG. 17, a perspective view of an alternative connector 376 is shown. Similar to the embodiment shown in FIGS. 15 and 16, the hose 352 has a plurality of channels 354 and 356 and allows air flow in both directions. However in contrast to the embodiment shown in FIGS. 15 and 16, the vent holes 368 are located on the connector 376 at the end of the hosepipe of the hose 352. FIG. 18 is a sectional view of the connector 376 of FIG. 17 taken along the line 18-18. The connector 376 has a blockage 366 that prevents flow in the other communication channel 356 from reaching the flow generator 22. One potential benefit is that the hosepipe, such as the hosepipe 314 shown in FIG. 14C can be used for both one direction flow and two direction flow dependent on the type of connector attached to the hosepipe.

Figure 19:
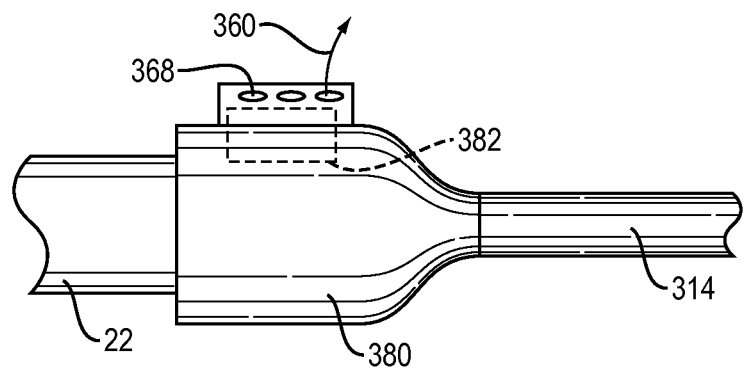
FIG. 19 is a side view of an alternative hose.

Referring to FIG. 19, a side view of an alternative hose connector 380 is shown. The connector 380 which is located at the flow generator 22 of the hosepipe and has the vent holes through which the exhaust gas flows as represented by arrow 358, has an acoustic suppression portion 382. The acoustic suppression portion 382 can have properties similar to those described above with respect to FIG. 3.

Figure 20:
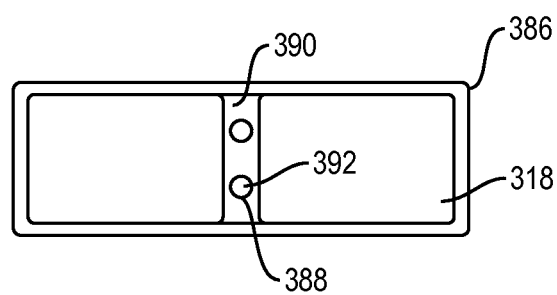
FIG. 20 is a sectional view of a hose with heating elements.

Referring to FIG. 20, a sectional view of a hose 386 with a plurality of heating elements 388 is shown. The hose 386 has a center rib or wall 390 with a pair of channels 392 through which the heating elements 388 extend. The heating elements 388 radiate heat into the air flow channels 318. The elements 388 are connected to a power source within the flow generator 22 through the tube connector. The elements 338 are activated during treatment to prevent condensation of humid gas within the air flow channels 318.

Figure 21A:
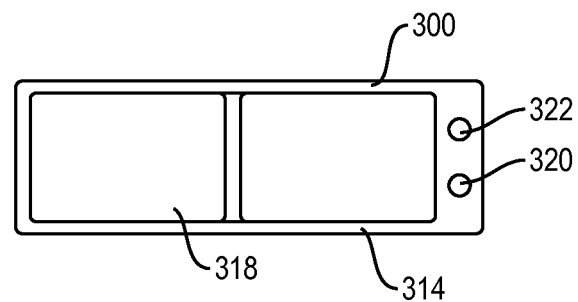
FIG. 21A is a sectional view of a hose with control wires.

Referring to FIG. 21A, a sectional view of a hose 200 with a pair of control apertures 320 and 322 is shown. The hose 200 is similar to the hose shown in FIGS. 14A-14C. The control apertures 320 and 322, as referred to as sampling channels, are used to communicate pneumatic signals between the mask 180 and flow generator 22. These pneumatic signals can be used to assist in the control of the system. For example, pressure readings may be sampled at the mask 180 and transmitted back to a controller located in the flow generator 22 through the mask connector 194, as seen in FIGS. 6 and 13, to the smaller communication channel 320 or 322 embedded in the hosepipe 314 of the hose 200. The signal is sent to a pressure sensor located in the flow generator 22 and then to the controller. The sensor readings assist the flow generator control in controlling the operating algorithm. The smaller channel can be formed during the extrusion processes. The controlling of the flow generator through pressures on the mask is further described in U.S. patent application Ser. No. 13/452,823 filed on Apr. 20, 2012, which is incorporated herein by reference.

Figure 21B:
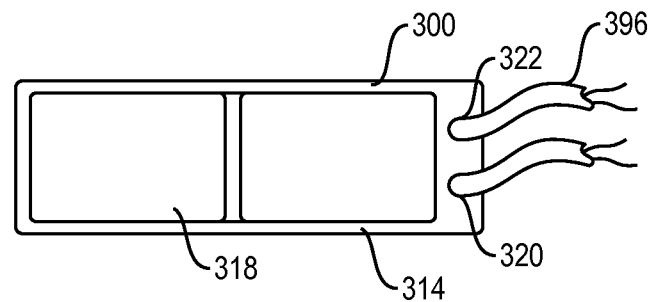
FIG. 21B is a sectional view of a hose with a control aperture.

Referring to FIG. 21B, a sectional view of a hose 200 with a pair of control wire channels 320 and 322 is shown. In the embodiment, each channel 320 and 322 has a pair of embedded wires 396. The wires 396 can be embedded during the extrusion process. The wires 396 are used to transmit electrical signals between the mask 180 and the flow generator 22. These electrical signals can be used to operate controls, indicator lights, and sensors, among others. For example, pressure readings with a pressure sensor may be sampled at the mask and transmitted back to the flow generator control through the mask connector, to the wires embedded in the tube, through the flow generator connector and to the flow generator control. The sensor readings assist the flow generator control in controlling the operating algorithm.

Figure 22A:
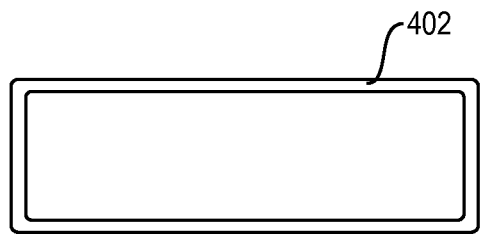
FIG. 22A is a sectional view of a hose with one channel.

FIG. 22A is a sectional view of a hose 402 with one channel; the hose is a low profile, generally rectangular-shaped tube which contains a single interior channel. The tube is extruded from flexible bio-compatible silicone or like material.

Figure 22B:
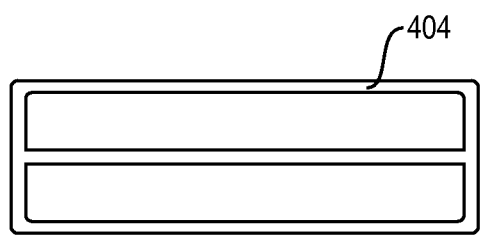
FIG. 22B is a sectional view of a hose with a pair of channels.

Referring to FIG. 22B, a sectional view of a hose 404 with a pair of channels is shown. The hose has a web that extends horizontally. While not shown, it is recognized that communication channels could be added to the side of the hose such as shown in FIGS. 21A and 21B.

Figure 22C:
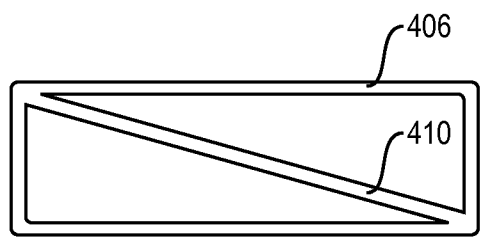
FIG. 22C is a sectional view of a hose with a pair of channels.

Referring to FIG. 22C, a sectional view of a hose 406 with two channels is shown. The hose has a web 410 that extends diagonally.

Figure 22D:
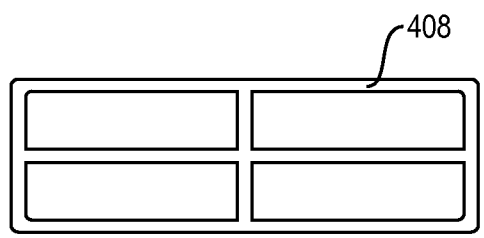
FIG. 22D is a sectional view of a hose with four channels.

Referring to FIG. 22D, a sectional view of a hose 408 with four channels is shown.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

It is recognized that in addition to obstructive sleep apnea (OSA) which may occur when the body relaxes during sleep, and the upper airway of the sleeping individual collapses, either partially or completely, to obstruct breathing during sleep, the system can address other conditions such as hypopnea and central sleep apnea (CSA). Hypopnea, another form of apnea, is exhibited by shallow and slow breathing during sleep.

What is claimed is:

1. A gas delivery system that provides positive airway pressure therapy during a user's sleep period, the system comprising:
   a mask being configured to couple to a user's face and being configured to deliver pressurized gas to an airway of the user;
   the mask further comprising:
      a flow generator system that pressurizes gas, the flow generator system including at least one motor;
      at least one washout vent that allows fluid communication, separately from the flow generator system, between an exterior of the mask and an interior of the mask;
      at least one unassisted breathing vent that allows fluid communication between an exterior of the mask and the interior of the mask, the fluid communication between the interior and exterior of the mask being separate from the fluid communication between the interior and exterior of the mask provided by the flow generator system and the at least one washout vent;
      a check-valve that obstructs the at least one unassisted breathing vent during operation of the flow generator; and
      a heat moisture exchange located on an interior of the mask through which the air from the flow generator system passes to condition the gas for the user.

2. A gas delivery system of claim 1, further comprising a heat moisture exchange (HME), the check-valve moves to a position therein redirecting the path of the air from the flow generator system through the HME and a second position wherein the air from the at least one unassisted breathing vent bypasses the HME.

3. A gas delivery system of claim 1, wherein the check-valve moves between a compressor mode position blocking the at least one unassisted breathing vent and a free breathing position blocking the outlet from the flow generator.

4. A gas delivery system of claim 3, wherein the check-valve is biased to the free breathing position blocking the outlet from the flow generator and forced to the compressor mode position by the pressure from the flow generator.

5. A gas delivery system of claim 1, wherein the flow generator is embedded into the mask.

6. A gas delivery system of claim 1, wherein the flow generator is spaced from the mask, and a hose is interposed between the flow generator and the mask for conveying pressurized gas to the mask.

7. A gas delivery system of claim 6, wherein the check-valve is located within the mask.

8. A gas delivery system of claim 1, wherein the washout vent area is less than 20 percent of the area of the at least one unassisted breathing vent.

9. A method of treating sleep apnea of a user comprising:
   providing a mask having a seal to engage a face of the user defining a cavity adapted to overlie at least one of the user's mouth and user's nose, a port for receiving pressurized gas, and a wash out venting of gases to the exterior including carbon dioxide;
   communicating of gas from the cavity to the exterior through at least one unassisted breathing vent;
   pressurizing the gas with a flow generator and delivery to the cavity for positive airway pressure (PAP) therapy to the user;
   closing of the at least one unassisted breathing vent by moving a check-valve to obstruct the at least one unassisted breathing vent during operation of the flow generator;
   moving of the check-valve to a second position allowing communicating of gas from the cavity to the exterior through at least one unassisted breathing vent when the flow generator is turned off; and
   conditioning the gas for the user with a heat moisture exchange located on an interior of the mask through which the air from the flow generator system passes prior to entering the user's mouth or nose.

10. A method of treating sleep apnea of claim 9, further comprising a heat moisture exchange (HME), the check-valve moves to a position therein redirecting the path of the air from the flow generator system through the HME and a second position wherein the air from the at least one unassisted breathing vent bypasses the HME.

11. A method of treating sleep apnea of claim 9, wherein the check-valve moves between a compressor mode position blocking the at least one unassisted breathing vent and a free breathing position blocking the outlet from the flow generator.

12. A method of treating sleep apnea of claim 11, wherein the check-valve is biased to the free breathing position blocking the outlet from the flow generator and is forced to the compressor mode position by the pressure from the flow generator.

13. A method of treating sleep apnea of claim 9, wherein the flow generator is embedded into the mask.

14. A method of treating sleep apnea of claim 9, wherein the flow generator is spaced from the mask, a hose interposed between the flow generator and the mask for conveying pressurized gas to the mask.

15. A method of treating sleep apnea of claim 14, wherein the check-valve is located within the mask.

16. A gas delivery system that provides positive airway pressure therapy during a user's sleep period, the system comprising:
   a flow generator system that pressurizes a breathable gas, the flow generator system including at least one motor;
   a mask being configured to couple to a user's face and being configured to deliver the pressurized breathable gas to an airway of the user, the mask further comprising:
      at least one washout vent that allows fluid communication, separately from the flow generator system, between an exterior of the mask and an interior of the mask;
      at least one unassisted breathing vent that allows fluid communication between an exterior of the mask and the interior of the mask, the unassisted breathing vent being biased to open to the exterior of the mask when the flow generator is off and configured to close when the flow generator is supplying the compressed breathable gas;
      a heat moisture exchange located on an interior of the mask, and wherein the compressed breathable gas from the flow generator system must pass through the heat moisture exchange prior to entering the user's airway; and an air supply hose connecting the flow generator to the mask.

* * * * *